United States Patent [19]

Boos

[11] Patent Number: 5,126,570
[45] Date of Patent: * Jun. 30, 1992

[54] SENSOR AND METHOD FOR MEASURING ALCOHOL CONCENTRATION IN AN ALCOHOL-GASOLINE MIXTURE

[75] Inventor: Donald L. Boos, Garfield Hts., Ohio

[73] Assignee: The Standard Oil Company, Cleveland, Ohio

[*] Notice: The portion of the term of this patent subsequent to Jun. 23, 2009 has been disclaimed.

[21] Appl. No.: 249,863

[22] Filed: Sep. 27, 1988

[51] Int. Cl.⁵ .......................................... G01N 21/35
[52] U.S. Cl. .................................. 250/343; 250/339; 250/345; 250/346; 123/1 A
[58] Field of Search ............... 250/339, 343, 346, 345; 356/436, 437, 407, 320, 51; 123/1 A, 494

[56] References Cited

U.S. PATENT DOCUMENTS

| | | | |
|---|---|---|---|
| 2,790,081 | 4/1957 | Munday | 250/343 |
| 2,852,693 | 9/1958 | Hughes et al. | |
| 3,729,264 | 4/1973 | Simazaki et al. | 250/345 |
| 4,286,327 | 8/1981 | Rosenthal et al. | 364/498 |
| 4,296,324 | 10/1981 | Kern et al. | 250/339 |
| 4,297,579 | 10/1981 | Spaeth | 250/343 |
| 4,383,181 | 5/1983 | Roess et al. | 356/320 |
| 4,391,253 | 7/1983 | Ito et al. | |
| 4,503,994 | 3/1985 | Pyle | 250/577 |
| 4,567,366 | 1/1986 | Shinohara | 250/339 |
| 4,577,970 | 3/1986 | Meserol | 356/246 |
| 4,587,427 | 5/1986 | Talbot et al. | 250/339 |
| 4,594,510 | 6/1986 | Brown et al. | 250/339 |
| 4,594,968 | 6/1986 | Degobert et al. | 123/1 A |
| 4,596,931 | 6/1986 | Ehnholm et al. | 250/343 |
| 4,647,776 | 3/1987 | Kern et al. | 250/339 |
| 4,749,274 | 6/1988 | Aoki et al. | 356/136 |
| 4,770,129 | 9/1988 | Miyata et al. | 123/1 A |
| 4,771,176 | 9/1988 | Schiefer et al. | 250/339 |
| 4,772,790 | 9/1988 | Aldridge | 250/343 |
| 4,800,279 | 1/1989 | Heiftje et al. | 250/339 |
| 4,808,825 | 2/1989 | Miyatake et al. | 250/343 |

FOREIGN PATENT DOCUMENTS

| | | |
|---|---|---|
| 0245512 | 5/1987 | European Pat. Off. |
| 0304232 | 2/1989 | European Pat. Off. |
| 53-97491 | 8/1978 | Japan ............................ 250/343 |
| 8004071 | 7/1981 | Netherlands. |
| 1040046 | 8/1966 | United Kingdom. |
| 2008745 | 6/1979 | United Kingdom. |
| 2053466 | 2/1981 | United Kingdom. |
| 2136118 | 9/1984 | United Kingdom. |
| 0285251 | 10/1988 | United Kingdom. |

OTHER PUBLICATIONS

Dovaud, "Le Moteur Souple", 2114 Petrole et Entreprise (1985) Juillet, No. 24, Paris, France.
Fraim et al, "Natural Gas Heating Valves Determination Using an Infrared Colorimeter".
Schmitz et al, "Intelligent Alcohol Fuel Sensor".
Dexter Research Center Technical Description—Model 2M Thermopile Detector—Aug. 1986.
Dexter Research Center Technical Description—Model DR46 Dual Element Thermopile Detector—Aug. 1986.
Van der Weide et al, "A Retrofittable Alcohol/Petrol Carburation System", Fourth International Symposium on Alcohol Fuels Technology, Oct. 5-8, 1980.
Joint Presentation "Vehicle Operation with Variable Methanol/Gasoline Mixtures", VI International Symposium on Alcohol Fuels Technology, Ford Motor Co., Ottawa, May 21/25, 1984.

*Primary Examiner*—Carolyn E. Fields
*Attorney, Agent, or Firm*—Larry W. Evans; Joseph G. Curatolo; Scott A. McCollister

[57] ABSTRACT

A sensor and method for measuring the concentration of alcohol in an alcohol-hydrocarbon mixture for use with flexible fuel vehicles. The sensor and method are characterized by a pair of detectors or sensing elements which detect absorbance of two different wavelength bands of energy transmitted through the fuel. The first wavelength band is absorbed by the alcohol and substantially unabsorbed by the hydrocarbons and other non-alcohols in the fuel mixture. The second or reference wavelength band is selected where the absorbance of alcohols and hydrocarbons is essentially the same and preferably essentially zero. The output of the two detectors or sensing elements is ratioed to provide a signal representative of the alcohol content of the fuel mixture. In a preferred embodiment, the sensing elements are included in a differential thermopile.

28 Claims, 5 Drawing Sheets

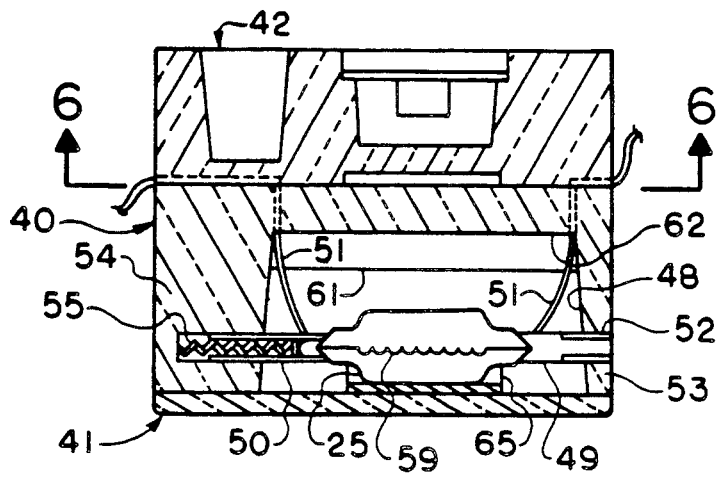
FIG. 5
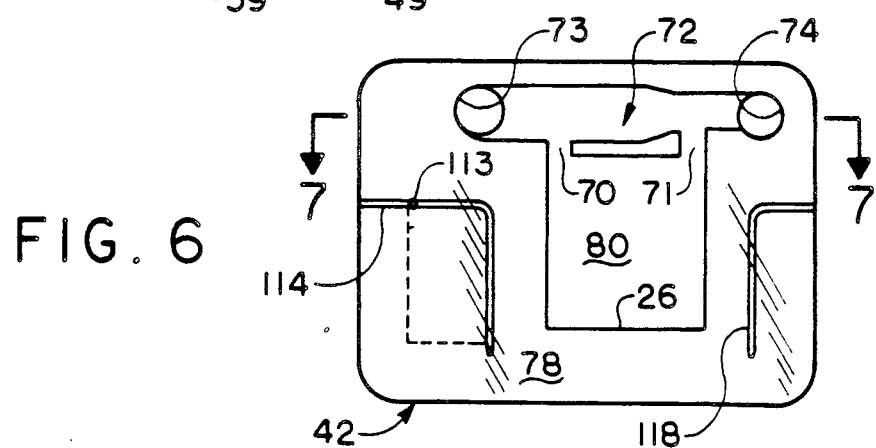
FIG. 6
FIG. 7
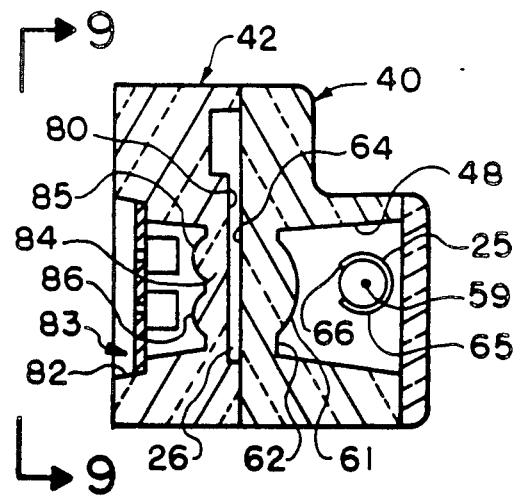
FIG. 8

SENSOR AND METHOD FOR MEASURING ALCOHOL CONCENTRATION IN AN ALCOHOL-GASOLINE MIXTURE

The invention herein described relates to a sensor and method for measuring the concentration of alcohol in alcohol-hydrocarbon mixtures. The sensor and method have particular application in a fuel supply system for fuels including alcohol, such as methanol or ethanol, and gasoline, or mixtures thereof.

BACKGROUND OF THE INVENTION

Alcohols have known potential for use as an alternative fuel for transportation vehicles. In addition to the realization that the world's petroleum reserves are finite and have only a relatively short life at present rates of consumption, environmental concerns and national security issues also serve to promote the use of alcohol (mainly ethanol and methanol) as a clean burning, high octane gasoline extender or replacement. Methanol is perhaps the most likely candidate to replace crude oil based liquid fuels.

The establishment of alcohol fuel distribution systems which provide a wide geographical spread of outlets will take considerable time to develop, as will replacement of automobiles and other transportation vehicles powered by engines designed to burn only gasoline. This conversion or transition to alcohol fuel, such as neat methanol fuel, would be facilitated by a methanol fueled vehicle that can operate satisfactorily using gasoline, methanol (or other alcohol) or any mixture of gasoline and alcohol(s). However, spark ignited engines require for proper combustion an air-fuel ratio for gasoline which is substantially different than the air-fuel ratio for methanol or ethanol. The problem is further complicated by mixtures of gasoline and alcohol which have a stoichiometric ratio that varies with the composition of the mixture.

Accordingly, a need exists for a sensor that may be used in a fuel system of an automobile or other vehicle that can measure the proportion of alcohol in the fuel and provide a representative signal for controlling the air-fuel ratio. The function of the fuel system would be to control the quantity of fuel delivered based on the mass of air inducted by the engine and the fuel composition as detected by the sensor. Auto makers have developed various mechanisms and controls for adjusting the air-fuel ratio in response to a signal from a fuel composition sensor. Most likely such adjustment would be controlled by an on board computer programmed to adjust automatically the air-fuel ratio in response to a signal from the fuel composition sensor. The computer might also control other operating parameters of the engine in response to the sensor output such as ignition timing.

Several infrared fuel composition sensors have been developed and/or proposed. U.S. Pat. No. 4,594,968 describes a device for determining the composition of an alcohol-gasoline mixture for use in the automatic regulation of engines fed with fuel mixtures having a variable alcohol content. The sensor uses a diode emitting a light beam in the infrared range having an average wavelength of 940 nanometers. The beam is divided into two parts by a semi-reflecting separating plate. One part of the beam passes to a first phototransistor through a measuring cell while the other part of the beam passes to a second phototransistor through a reference cell containing a reference liquid of known composition such as pure methanol. The phototransistors are connected to the two inputs of a differential amplifier which provides a measurement signal assumed to be representative of the methanol percentage.

In addition to the above noted sensor based on infrared absorbance, other proposed or investigated sensors have been based on index of refraction, ultrasonic sound or index of refraction. These prior art sensors suffer from one or more drawbacks including sensitivity to temperature, fuel flow, impurities, mixture inhomogeneities, environmental temperature constrains, reliability, complexity and cost.

SUMMARY OF THE INVENTION

The present invention provides a sensor and method for measuring the concentration of alcohol in alcohol-hydrocarbon mixtures. The sensor and method of the invention overcome or minimize one or more drawbacks associated with known fuel composition sensors and methods developed or proposed for use in vehicle engine fuel systems. The sensor and method are characterized by a pair of detectors or sensing elements which detect absorbance of two different wavelength bands of energy transmitted through the fuel. The first wavelength band is selected so that absorbance thereof will be proportional to alcohol content of the fuel mixture; the first wavelength band is absorbed by the alcohol and substantially unabsorbed by the hydrocarbons and other non-alcohols in the fuel mixture. The second or reference wavelength band is selected where the absorbance of alcohols and hydrocarbons (non-alcohols) is essentially the same and preferably essentially zero. The output of the two detectors or sensing elements provides a signal related to the alcohol content of the fuel mixture.

According to one broad aspect of the invention, a sensor for measuring the amount of alcohol in an alcohol-gasoline fuel mixture comprises means for generating a broad band of energy including a first wavelength band of energy that will be absorbed by the alcohol and substantially unabsorbed by the gasoline and a second wavelength band of energy that will be absorbed substantially equally by the alcohol and gasoline; means for receiving the alcohol-gasoline fuel mixture for passage of the first and second wavelength bands of energy through the mixture; and means for detecting the amount of energy remaining in the first and second wavelength bands of energy passed through the alcohol-gasoline mixture and for providing a signal proportional to the difference between the detected amounts of energy.

In the preferred embodiment, the means for detecting includes a differential thermopile having first and second sensing elements. First and second band pass filters are disposed between the means for generating and the first and second sensing elements, respectively, for passing the first and second wavelength bands to the sensing elements, to the extent such first and second wavelength bands are not absorbed during passage through the alcohol-gasoline mixture. In the preferred embodiment for measuring, in particular, the methanol content of a methanol-gasoline mixture, the first wavelength band preferably is a band centered at about 1550 nm and the second wavelength band is a band centered at about 1300 nm.

According to another broad aspect of the invention, a sensor for measuring the amount of alcohol in an alcohol-gasoline mixture comprises means for generating a wide band of energy including a first wavelength band of energy that will be absorbed by the alcohol and substantially unabsorbed by the gasoline and a second wavelength band of energy that will be absorbed substantially equally by the alcohol and gasoline; means for receiving the alcohol-gasoline mixture for transmission of the first and second wavelength bands of energy through the mixture; and first and second detector means respectively for detecting the amount of energy remaining in the first and second wavelength bands of energy transmitted through the alcohol-gasoline mixture.

In the preferred embodiment, the aforesaid means for receiving preferably is a narrow flat walled chamber which is connected at its upper end by respective passages to the inlet and outlet of a venturi connected in line with the fuel line through which the alcohol-gasoline fuel mixture passes. The venturi continuously draws the fuel mixture into the chamber for measurement of the alcohol concentration. The means for generating in the preferred embodiment preferably is an incandescent lamp operating at less than rated voltage to extend lamp life and minimize the amount of heat generated by the lamp. The preferred embodiment further is characterized by a reflector and lenses for efficient passage of the wavelength bands of energy through the sampling chamber and collection by the detecting means. The invention also provides electronic circuitry for amplifying and/or conditioning the output of the detectors for remote transmission to data processing means such as the onboard computer of a vehicle which may operate to adjust one or more parameters of the vehicle's engine in response to the output of the sensor.

The invention also provides a method for measuring the amount of alcohol in an alcohol-gasoline fuel mixture, the method comprising the steps of generating a broad band of energy including a first wavelength band of energy that will be absorbed by the alcohol and substantially unabsorbed by the gasoline and a second wavelength band of energy that will be absorbed substantially equally by the alcohol and gasoline; passing the first and second wavelength bands of energy through the alcohol-gasoline fuel mixture; and detecting the amount of energy remaining in the first and second wavelength bands of energy passed through the alcohol-gasoline mixture and providing a signal proportional to the difference between the detected amounts of energy.

Although the invention is summarized above in the context of an improved sensor and method for determining the alcohol and, in particular methanol, content of an alcohol(methanol)-gasoline fuel mixture, the principles of the invention may also be applied to other sensors and methods for determining the amount of an energy absorbing compound in a mixture thereof with other energy absorbing compounds. In this more general application, the comparison will be between transmitted radiation in a wavelength band which is absorbed by the measured energy absorbing compound and not by the other compounds and a wavelength band which is equally absorbed by the measured and other compounds and preferably substantially unabsorbed by such compounds. It also will be appreciated that various aspects of the invention may have application in other types of sensors and sensing methods of various types.

The invention comprises the foregoing and other features hereinafter fully described and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

In the annexed drawings:

FIG. 5 is a horizontal sectional view of the sensor taken along the line 5—5 of FIG. 4;

FIG. 6 is a vertical sectional view of the sensor taken along the line 6—6 of FIG. 5;

FIG. 7 is a horizontal fragmentary sectional view of the sensor taken along the line 7—7 of FIG. 6;

FIG. 8 is a vertical sectional view of the sensor taken along the line 8—8 of FIG. 4;

DETAILED DESCRIPTION

Figure 1:
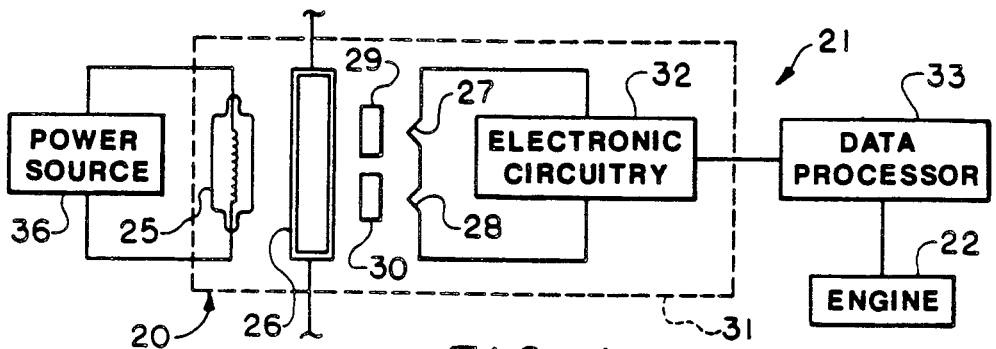
FIG. 1 is a combination block and schematic diagram of a sensor system embodying the principles of the present invention.

Referring now in detail to the drawings and initially to FIG. 1, a sensor for determining the methanol content of a methanol-gasoline fuel mixture is schematically indicated at 20. Sensor 20 is shown in diagrammatic relation to other components of a system 21 for automatically in adjusting one or more parameters of an internal combustion engine 22 response to the methanol content of the fuel as measured by the sensor. In this detailed description focus primarily will be on methanol-gasoline fuel mixtures since methanol is perceived to be the most likely replacement fuel for gasoline and other crude oil based liquid fuels. However, the invention may be practiced with other alcohol-hydrocarbon mixtures including, in particular, ethanol-gasoline fuel mixtures. The invention also will be described as implemented in a vehicle powered by internal combustion engine 22.

Sensor 20 generally comprises a light source 25, a sampling chamber 26, a pair of detectors 27 and 28, and respective filters 29 and 30 for the detectors. These components are disposed in a housing indicated by broken lines at 31. The sensor further comprises electronic circuitry 32 which amplifies the output of detectors 27 and 28 for remote transmission to a data processor 33. The function of the data processor is to control one or more parameters of engine 22. The data processor may be connected to a display to provide a visual read-out of methanol concentration.

Data processor 33 may be the vehicle's on board computer programmed to adjust automatically the air-fuel ratio in response to the output of sensor 20. In this manner the air-fuel ratio may be optimized for any given mixture of methanol and gasoline (octane and other hydrocarbons, the gasoline may also include additives such as octane enhancers) being supplied to engine 22. Various computerized systems for adjusting the air-fuel ratio in response to a signal from a fuel composition sensor heretofore have been developed and sensor 20 may be conventionally employed in such systems in place of known fuel composition sensors, although with improved results resulting from improved performance and characteristics of sensor 20, as detailed below.

Referring now to details of the components and operation of sensor 20, light source 25 preferably is an inexpensive broad band incandescent lamp energized by a stable, well regulated DC power source 36. Lamp 25 generates a broad band of light including, in particular, near infrared light or energy which is beamed or transmitted through the sampling chamber 26. Preferably the lamp is powered at a voltage less than its rated voltage to extend its life. For example, a 12.8 volt rated automotive dome lamp may be operated at 9.0 volts to obtain an anticipated 3500% increase in life at the cost of an anticipated 10% loss of infrared light in the hereinafter identified band regions.

Sampling chamber 26 preferably is a flat walled cell which receives fuel from fuel line 37 of the vehicle. Light emerging from the sampling chamber impinges upon detectors 27 and 28 after passing through filters 29 and 30, respectively. Detectors 27 and 28 are situated so that the path lengths of light from the light source to each detector are constant and the same as each other. As depicted, the detectors are positioned in side-by-side relationship in symmetrical relation to light source 25, and the filters are similarly disposed to cover the sensing areas of the detectors.

Filters 29 and 30 are band pass filters which permit only a limited or narrow band of energy to impinge upon detectors 27 and 28. A narrow band of energy herein means a band of energy including only a single wavelength or closely grouped wavelengths. The narrow band width preferably ranges from about 12 nm to about 100 nm, with a narrow band width of about 60 nm being most preferred. However, larger band widths could still be used, as further discussed below. On the other hand, a broad band of energy is one which includes many wavelengths over wide range.

More particularly, filter 29 is a 1550 nm band pass filter having a band width of 60 nm (centered at 1550 nm). This wavelength band is absorbed by methanol and substantially unabsorbed by the hydrocarbons and other non-alcohols typically found in gasoline fuels; accordingly, the absorbance of this wavelength band by a methanol-gasoline fuel mixture is proportional to the methanol content of the fuel. The other filter 30 is a 1300 nm narrow band pass filter having a band width of 60 nm (centered at 1300 nm). Absorption of this wavelength by methanol and typical gasoline hydrocarbons and non-alcohol additives is essentially zero and, more importantly, substantially the same.

Detectors 27 and 28 will detect the amount of energy remaining in the selected wavelength bands and provide outputs proportional thereto. These outputs are ratioed to provide a signal representative of the methanol content of the fuel mixture. As above discussed, this signal, the sensor output, is transmitted to the vehicle's on board computer 33 where, for example, lookup tables may be used to determine the methanol concentration from the sensor output signal.

As will be appreciated, this dual sensor approach makes sensor 20 insensitive to contaminants, which has been a problem with some prior art schemes. This is because both detectors see the same fuel. Moreover, changes in source intensity due to lamp aging, cloudy fuel or dyes will be detected by the two detectors simultaneously; accordingly the ratio of their outputs will remain unchanged.

Figure 2:
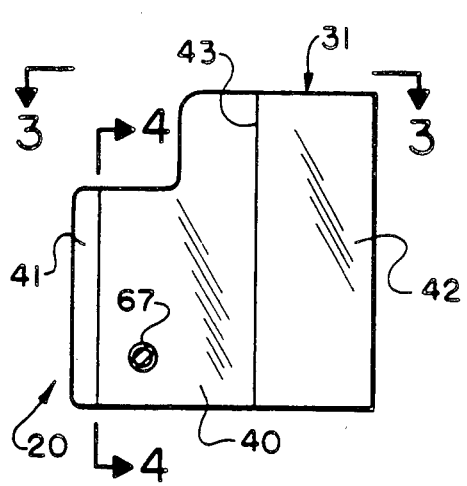
FIG. 2 is an end elevational view of a sensor according to the present invention.
Figure 3:
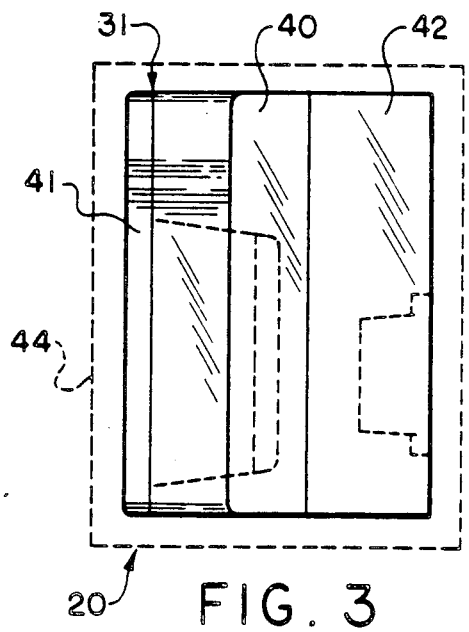
FIG. 3 is a top plan view of the sensor looking from the line 3—3 of FIG. 2.

Now referring to FIGS. 2-9, components of sensor 20 are shown in greater detail. As seen in FIGS. 2 and 3, housing 31 of sensor 20 is an assembly comprising lamp housing 40, lamp cover 41 and detector housing 42. This multi-part assembly facilitates fabrication of the sensor 20. Lamp housing 31 and detector housing 42 are permanently joined together at parting line 43 by cement or other suitable means to form a unitary housing body. Lamp cover 41, on the other hand, is removably attached to the lamp housing by removable screw fasteners or other suitable means (not shown) to permit easy replacement of the light source 25 which can be seen to be an incandescent lamp in FIGS. 4 and 5.

Lamp housing 40, lamp cover 41 and detector housing 42 are made of polysulfone as is preferred for use with methanol-gasoline fuel mixtures. However, other materials may also be useful such as PET and epoxy. Generally the material must be transparent or at least transluscent to the selected wavelength bands and should have high chemical resistance to the fuel mixture components. Also, the material should be capable of withstanding the heat generated by the lamp as well as environmental temperatures which may be encountered.

Housing assembly 31 may be contained in a casing schematically illustrated by broken lines at 44 in FIG. 3. The casing may be formed of aluminum or other suitable metal to provide EMF shielding. The casing may also be adapted as needed for mounting in a vehicle, such as by being provided with mounting brackets and/or other suitable mounting hardware. Typically these requirements would be specified by the vehicle manufacturer. The casing preferably is opaque and sealed against entry of light thereby to shield the sensor from environmental light.

Figure 4:
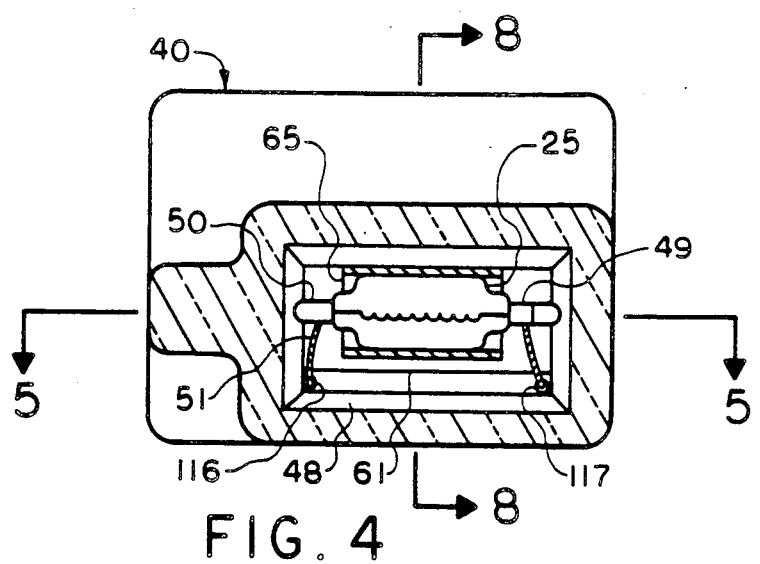
FIG. 4 is a vertical sectional view of the sensor taken along the line 4—4 of FIG. 2.

As seen in FIGS. 4 and 5, lamp housing 40 has a receptacle 48 which opens to the outer side of lamp housing (the side remote from the detector housing 42). Light source 25 in the form of an incandescent lamp may be retained in the receptacle by any suitable means. In the illustrated embodiment, the lamp is retained in receptacle 48 by opposed lamp holders 49 and 50 which also function as electrical terminals for connecting the lamp to a power source. The lamp holders have electrical leads 51 which are attached thereto and which extend from the lamp housing for connection to the power source 36 (FIG. 1). The leads preferably are passed out of the lamp housing generally in the manner discussed hereinafter.

The illustrated lamp holders 49 and 50 are axially opposed to one another and coact to hold lamp 25 therebetween. Lamp holder 49 is retained in sleeve 52 which is fitted in a bore in the side wall 53 of the lamp housing. The other lamp holder 50 is movable in a bore in the opposite side wall 54 of the lamp housing and is resiliently biased by spring 55 towards lamp holder 49. Lamp holder 50 may be pushed to the left in FIG. 5 against the spring force to permit insertion of the lamp between the holders. After a lamp has been installed as shown lamp cover 41 may be secured to the lamp housing to close the open side of the receptacle to prevent dirt and moisture from entering the receptacle.

Lamp 25 is held in receptacle 42 such that its linear filament 59 extends along the focal line of a convex linear lens 61 formed on and preferably integrally with the inner wall 62 of the lamp housing at the bottom of receptacle 48, as best seen in FIG. 8. Lens 61 functions to converge the rays of light passing through it from right to left in FIG. 8 so that the rays passing from a planar inner surface 64 of the lamp housing extend in generally parallel relationship at right angles to such inner surface 64. More importantly the light rays will be spread so that they pass through sampling chamber 26 in a direction parallel to the thickness direction of the sampling chamber, i.e., in a direction perpendicular to the planar extent of the narrow sampling chamber.

Preferably, a reflector 65 is used to direct substantially all the light emitted by the lamp 25 towards the sampling chamber 26. The reflector 65 in the illustrated preferred embodiment is a sheet of aluminum foil. The aluminum foil reflector is wrapped around the outer cylindrical surface of the lamp and is secured to such surface by silicone cement, although other means may be used to secure the reflector. The reflector extends around the back side of the lamp and has opposed ends at the front side of the lamp which define a slit 66 facing the lens 61. The slit 66 is parallel to the filament of the lamp and allows light to escape towards the convex surface of lens 61. The width of slit 66 is selected to cast light across the width of lens 61 for subsequent passage through the operative area of sampling chamber 26.

The reflector, lamp and holder assembly provides for convenient calibration of the sensor. Calibration is desired to adjust for differences in spectral outputs of lamps and different responses of thermopiles from sensor to sensor. By rotating slit 66 about the axis of lamp 25, the relative amounts (intensity) of light passing to the filters may be varied. For example, slit 66 may be slightly rotated clockwise in FIG. 8 to direct a greater percentage of light energy towards the upper detector and lens and less towards the lower detector and lens. To calibrate, reflector 65 is rotated to position slit 66 so that the sensor provides a zero output for neat (100%) gasoline, i.e., zero methanol concentration, as is preferred.

In the illustrated embodiment, rotation of the reflector is effected by rotating lamp 25 about its axis, reflector 65 being secured to the lamp and thereby correspondingly rotated. To permit rotation of the lamp in the finished assembly, sleeve 52 is provided at its outer end with a slot 67 (FIG. 2). Slot 67 is accessible from outside the sensor housing. A screwdriver may be engaged in slot 67 to turn the lamp and reflector to zero the sensor output for zero methanol concentration. Calibration in this manner corrects for differences in spectral outputs of the lamps and different responses of thermopiles from sensor to sensor, so that the sensors will have the same output signal for the same concentration of methanol in the methanol-gasoline mixture.

As best seen in FIG. 6, sampling chamber 26 is generally rectangular in cross-section perpendicular to its thickness direction. At its top the sampling chamber is connected by horizontally spaced apart passages 70 and 71 to upstream and downstream ends of a venturi indicated at 72. The upstream and downstream ends of venturi 72 are connected to tapered connection ports 73 and 74, herein also referred to as inlet and outlet ports, respectively. The tapered connection ports provide for connection of the venturi in line with fuel line 37 (FIG. 1) of the vehicle.

As will be appreciated, flow of fuel through the fuel line and hence through venturi 72 will cause fuel to be drawn into sampling chamber 26. This use of a venturi minimizes the effects of turbulence, vaporized fuel and air bubbles that could distort the amount of light received by the detectors. Because passages 70 and 71 are connected to the upper end of the sampling chamber, air bubbles drawn into the sampling chamber will pass across the upper region of the chamber and therefore will not interfere with light passing from the light source to the detectors in the middle region of the sampling chamber.

In the illustrated embodiment, sampling chamber 26, passages 70 and 71, and venturi 72 are formed by recesses and channels in the inner surface 78 of the detector housing. The inner surface 78 of the detector housing surrounding the recesses and grooves is fastened by cement to mating inner surface 64 of the lamp housing. The inner surface of the lamp housing closes the open sides of the recesses and channels to form the sampling chamber, venturi and connecting passages.

The bottom 80 of one recess in the surface 78 forms one side or wall surface of sampling chamber 26 while the opposite side surface is formed by a corresponding portion of inner surface 64 of lamp housing 40. Side surfaces 80 and 64 preferably are smooth planar surfaces extending parallel to one another and perpendicular to the path of light rays therethrough. This minimizes scattering and internal reflection of the light rays at the solid-liquid interfaces for more efficient transmission of light through the sampling chamber.

Figure 9:
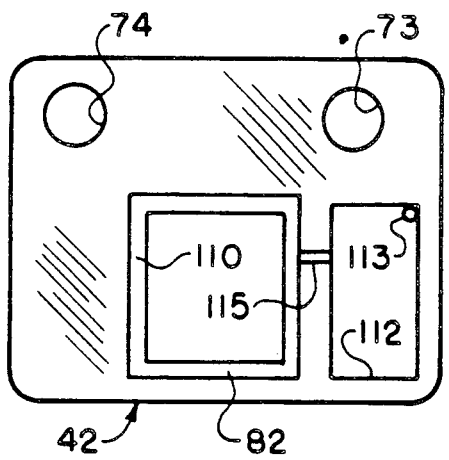
FIG. 9 is a side elevational view of the sensor looking from the line 9—9 of FIG. 8.

As seen in FIGS. 5, 8 and 9, detector housing 42 has a recess 82 for housing an assembly 83 including detectors 27, 28 and filters 29, 30. The recess 82 opens to the outer side of the detector housing and is aligned with sampling chamber 26 and lamp 25. A relatively thin wall 84 separates the recess from the sampling chamber. At its outer side forming the bottom of recess 82, wall 84 has formed thereon a pair of linear lenses 85 and 86. Lenses 85 and 86 are parallel and are located one above the other in symmetrical relationship with respect to a plane which intersects the axis of the lamp and is perpendicular to the planar extent of the sampling chamber. As will be seen, the detectors are similarly disposed so that the lengths of the light paths between the lamp and detectors will be the same.

The function of each lens 85, 86 is to converge light rays passing from the sampling chamber 26 onto the sensing area of the respective detector 27, 28. That is, the sensing area of the detector preferably is located at or about the focal point of the lens or, in the illustrated embodiment, at or about the focal line of the linear lens.

Before impinging on the sensing areas of detectors 27 and 28, the converging light rays pass through filters 29 and 30, respectively. As above indicated, filter 29 is a 1550 nm narrow band pass filter and the filter 30 is a 1300 nm narrow band pass filter. Although relatively narrow band pass filters are preferred, the invention can be practiced with broader band widths such as, for example, a 1450-1650 nm band for detector 27, herein referred to as the measuring detector, and a 1200-1400 nm band for detector 28, herein referred to as the reference detector.

Figure 10:
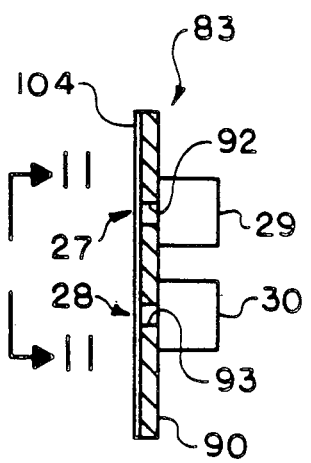
FIG. 10 is an enlarged edge view of a detector-filter assembly employed in the sensor.
Figure 11:
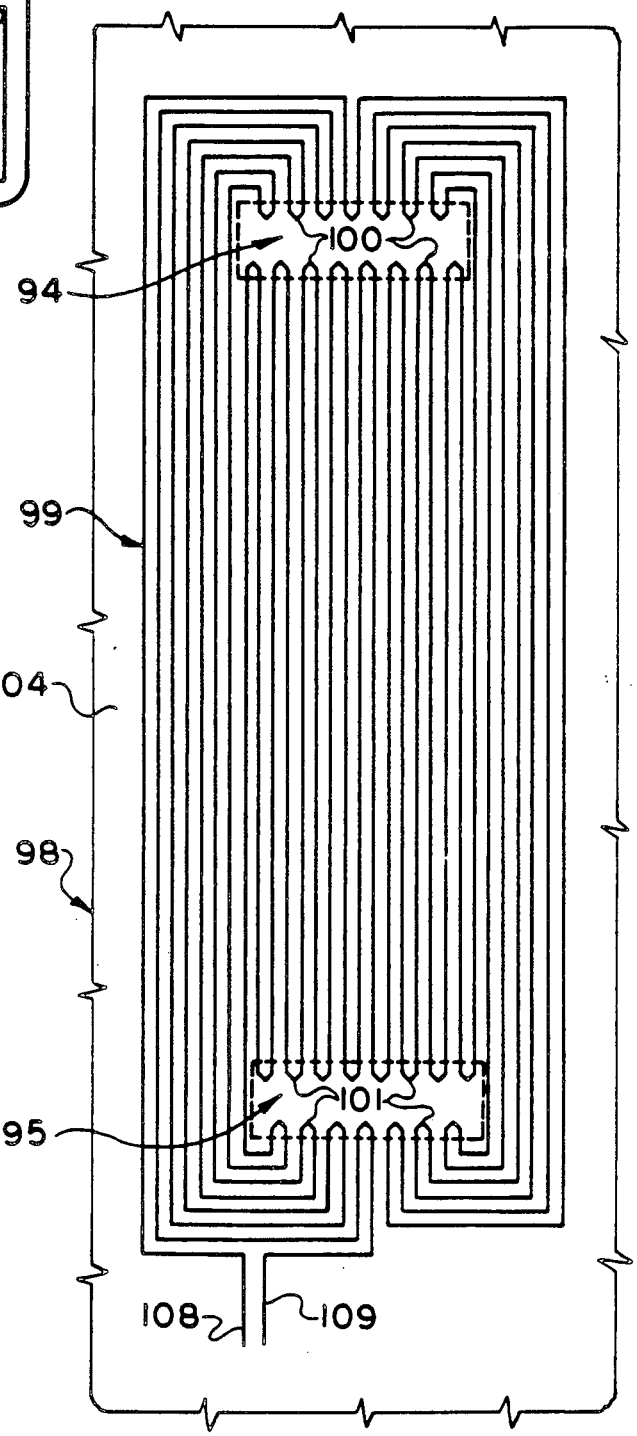
FIG. 11 is an enlarged view of the detector-filter assembly looking from the line 11—11 of FIG. 10.

In FIGS. 10 and 11, details of a preferred detector-filter assembly 83 are illustrated. Assembly 83 includes an aluminum plate 90 which forms a substrate to which filters 29 and 30 are mounted. As shown, filters 29 and 30 are in the form of chips which are cemented to the inner surface of the plate 90. Filters 29 and 30 cover respective openings 92 and 93 in the plate 90. The openings 92 and 93 are in the form of slits which define windows for passage of light rays through the plate 90 for impingement upon sensing areas of detectors 27 and 28, respectively.

In the preferred embodiment, detectors 27 and 28 are formed by the sensing elements 94 and 95 of a unique multi-junction dual element differential thermopile 98. As seen in FIG. 11, the dual element thermopile 98 includes a plurality of thermocouples generally indicated at 99 and the thermocouples are connected in series. Each thermocouple includes a hot thermojunction 100 and a cold thermojunction 101. The cold thermojunction of each thermocouple is connected to the hot thermojunction of the next series connected thermocouple by sharing of a common conductive element of the respective thermocouples, as is depicted in FIG. 11.

Dual element thermopile 98 is made by evaporating bismuth and antimony on a substrate 104 which is a thin Mylar polyester film in the illustrated embodiment. The antimony and bismuth are applied to the Mylar polyester film to form the conductive elements of the thermocouples arranged as illustrated in FIG. 11. The hot and cold junctions 100 and 101 are disposed in band-like areas which are laterally spaced apart and form respective sensing areas or elements 94 and 95. In each sensing area the thermojunctions are arranged into a pair of parallel rows as shown. An inner grouping of the thermocouples having their hot and cold junctions arranged in respective inner rows at the sensing areas and an outer grouping of thermocouples, generally surrounding the inner grouping, have their hot and cold junctions arranged in respective outer rows in the sensing areas. The dual element thermopile has output leads 108 and 109 which extend to mounting pads (not shown) to which respective leads are attached for connection of the dual element thermopile to the electronic circuitry 32 hereinafter described.

As seen in FIG. 10, the Mylar polyester substrate 104 of the thermopile 98 is affixed to the outer surface of the aluminum plate 90 by cement, although other suitable securement means may be employed if desired. Sensing areas 94 and 95, also herein referred to as the sensing elements, are located on the outer side of the Mylar polyester substrate and are aligned with respective ones of the window slits 92 and 93 (the relative position of the slits is outlined in broken lines in FIG. 11). In the regions of these window slits 92 and 93, the Mylar polyester substrate 104 has applied to its inner surface an energy absorbing material such as smoke black for efficient collection of the light energy impinging upon the sensing elements of the thermopile 98. It is desirable that the spectral absorption of the smoke black or other energy absorbing material be essentially flat in the selected wavelength bands of the light impinging upon the sensing areas of the thermopile.

As will be appreciated, the spectral band impinging upon each sensing area 94, 95 is limited by the corresponding filter 29, 30. As will be further appreciated, the voltage generated across the terminal leads 108 and 109 will be proportional to the difference between the radiative inputs, i.e., the radiation energies impinging upon the sensing elements. More particularly, the output of the thermopile 98 will range from a minimum corresponding to zero methanol content to a maximum corresponding to neat methanol.

Metal plate 90, in addition to serving as a support structure and windowing device for detector-filter assembly 83, provides for convenient mounting of assembly 83 in the detector housing 42. As seen in FIGS. 5 and 9, the inner portion of the recess 82 has a reduced cross-section forming a shelf or shoulder 110 inset from the outer surface of the detector housing. The outer peripheral area of metal plate 90 rests against shoulder 110 for proper positioning of assembly 83 in recess 82. Also, plate 90 is sized to fit closely in the larger cross-section outer region of recess 82 to prevent sideways shifting of the assembly thereby to maintain the assembly in proper alignment with respect to lenses 85 and 86, sampling chamber 26, lens 61 and lamp 25. The detector-filter assembly may be fixed in place by any suitable means such as by a press fit in the recess or by cementing to the shoulder. The outer side of the assembly preferably is protected from the environment by suitable means such as, for example, the provision of a protective casing 44. Silicone rubber may be used at the outer side of the assembly to hold the assembly in place and further provide environmental protection.

As further seen in FIG. 9, detector housing 42 has a second recess 112 laterally spaced from the recess 82. The recess 112 is used to accommodate a circuit board assembly embodying the electrical components schematically illustrated in FIG. 14. This circuit board assembly will be described in greater detail below, but it is here noted that the circuit has power supply and signal output leads (not shown). These leads are passed from recess 112 to the outside of housing 31 via a hole 113 and a passage formed by a groove 114. Hole 113 extends from the bottom of recess 112 to inner surface 78 of detector housing 42, and hole 113 intersects groove 114 formed in inner surface 78, as seen in FIGS. 5, 6 and 9. The circuit board assembly also is connected to detector assembly 83 by a pair of leads which may pass from recess 82 to recess 112 via a groove 115 formed in the outer surface of detector housing 42. It also can be seen in FIGS. 4, 5 and 6 that power leads 51 for lamp 25 may be passed from compartment 48 to outside the sensor housing via holes 116 and 117 and passages formed by grooves 114 and 118. The grooves 114 and 118 are formed in the inner surface 78 of detector housing 42. As will be appreciated, the various leads may be threaded through the holes and laid in the grooves before assembly of the housing parts. When the housing parts are secured together, the grooves are closed to form passages containing the several leads. It further is noted that the lamp compartment and the circuit board compartment or recess 112 are connected internally of the housing via hole 113, groove 114 and hole 116, as is preferred. This is advantageous especially when it is desired to use a common ground or reference line for both the lamp and detector circuits, thereby minimizing the number of external leads for the sensor.

Figure 12:
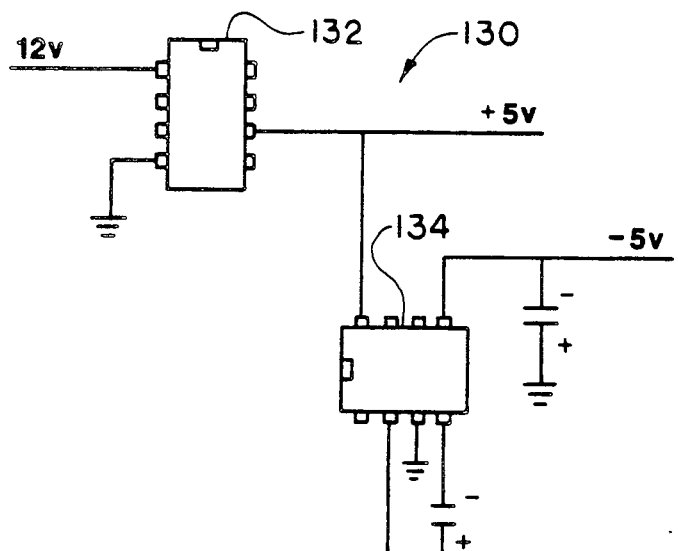
FIG. 12 is a circuit schematic for a reference voltage supply.

In FIG. 12, there is shown a circuit 130 for supplying plus and minus 5 volts from a 12-volt input. Such plus and minus 5 volts may be used in the other circuits described herein, e.g. as input, reference, bias and like voltages. The circuit employs in conventional manner an LM404 5-volt voltage reference supply 132 and an ICL7660 voltage converter 134 which are commercially available integrated circuits connected to provide a well regulated plus 5 output and a minus 5 volt output as are indicated in the drawing.

Figure 13:
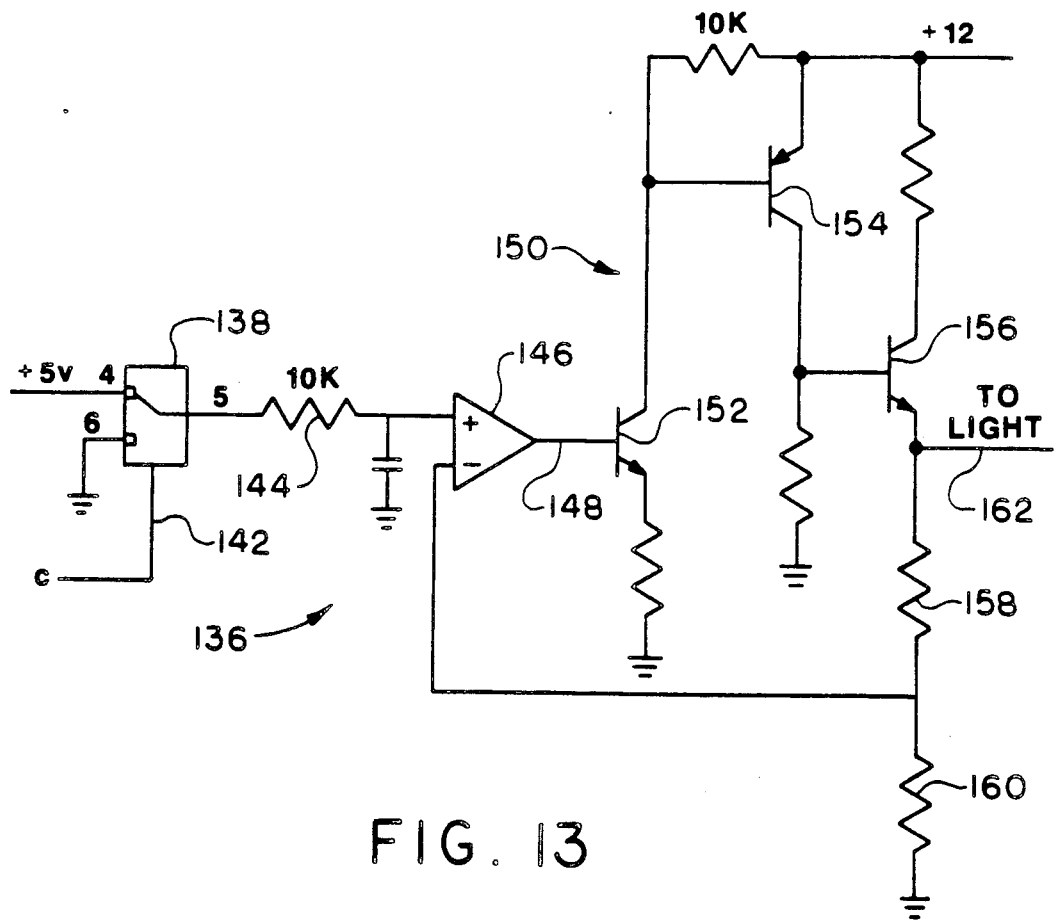
FIG. 13 is a circuit schematic for a power supply for a lamp employed in the sensor.

In FIG. 13, a circuit 136 for the power source 36 is illustrated. The circuit 136 provides a regulated supply voltage to lamp 25 and further functions to turn the lamp on and off. With the circuit 136, the lamp may be cycled on and off to extend lamp life and minimize the amount of heat generated by the lamp.

Voltage supply circuit 136 for the lamp includes an electronic switch 138, such as an MC54HC4353 electronic switch, which switches input between zero (or ground) and plus 5 volts in response to a signal, such as a periodic on/off signal from a free running oscillator, multivibrator or the like, to control input 142. The output 140 of electronic switch 138 is fed via an RC circuit 144 to the plus input of an operational amplifier 146 which may be an LM2902 op amp. The operational amplifier 146 functions to try to maintain a zero voltage differential between its plus and minus inputs. If the plus input is plus 5 volts, the signal produced at the output 148 will be of a nature that tries to function via the transistorized circuitry 150 to maintain 5 volts at its minus input.

The transistorized circuitry 150 includes transistors 152, 154 and 156 and a plurality of resistors illustrated. The minus input of operational amplifier 146 is connected to a voltage divider consisting of resistor 158 and resistor 160. In the illustrated embodiment, resistor 158 is a 376 ohm resistor and resistor 160 is a 470 ohm resistor. To maintain the minus input of operational amplifier 146 at minus 5 volts, the current through resistor 160 must be 10.64 milliamps (i.e., 5 volts/470 ohms). Assuming no current flows into the minus input of the operational amplifier, the same current must flow through resistor 158. Accordingly, the voltage drop across resistor 158 is 4 volts (i.e., 10.64 ma times 376 ohms) and the output 162 to the lamp is then at 9 volts (i.e. 5 volts +4 volts). However, when electronic switch 138 provides a zero input voltage to the plus input of operational amplifier 146, the output voltage to the lamp will be zero volts. The transistors 152, 154 and 156 respectively may be a ZN3904 signal transistor, a ZN3906 signal transistor and a BD241 power transistor.

The circuit 136 may be used when it is desired to turn lamp 25 on and off as when using higher wattage lamps. Higher wattage lamps may be preferred when using band pass filters having band widths on the order of about 12 nm to 20 nm. The higher wattage bulbs produce more light in the specified bands which in turn produces more signal in the detectors, as is desired.

A more preferred arrangement is the use of a low wattage lamp which may be energized continuously, i.e., not cycled on and off. For example, a miniature automotive lamp rated at 3 watts and 12.8 volts may be used and operated continuously at 9 volts, and one such lamp is a DE3022 miniature automotive lamp which is available from the General Electric Company. To provide a desirable detector output signal, band widths of from about 40 nm to about 100 nm are desired and preferably the band widths are about 60 nm for the measuring and reference detectors. Since the lamp is not cycled on and off, the lamp may be powered by a conventional voltage regulator providing a 9 volt output. The voltage regulator circuit may employ, for example, an LM317 voltage regulator.

Figure 14:
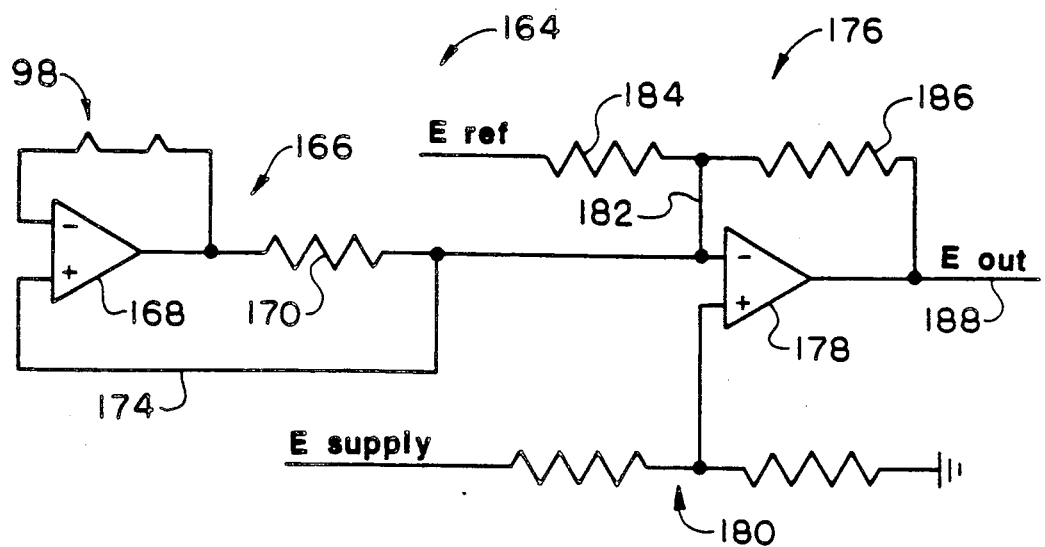
FIG. 14 is a circuit schematic for an output circuit for the sensor.

Referring now to FIG. 14, the differential thermopile 98 is connected in an amplifier circuit 164 of electronic circuitry 32. It is noted that the differential thermopile 98 employed to detect the difference in radiation between the two light paths provides a weak output signal on the order of 1 to 5 millivolts. Such a signal requires pre-amplification, which is provided by pre-amplifier 166 in amplifier circuit 164. In the preferred embodiment such pre-amplification is achieved by coupling the thermopile 98 in a current source circuit. Moreover, to avoid problems with noise pick-up the pre-amplifier should be located close to the thermopile. The thermopile can produce either a positive or negative voltage; therefore, the pre-amplifier 166 must be capable of operation with a positive and negative supply voltage or be biased at a voltage above ground. Since the automotive voltage supply is typically only positive, a biased amplifier preferably is used.

As seen at the left in FIG. 14, thermopile 98, which functions as an isolated voltage supply, is converted to a simple current supply by connection with operational amplifier 168 and using positive feed-back and a current sensing resistor 170 as shown. As shown, the thermopile is connected between the minus input and the output of the operational amplifier 168. The output of the operational amplifier also is connected across a current sensing resistor 170 to the plus input of the operational amplifier to provide the desired positive feedback. Thus, the pre-amplifier 166 is in the form of the illustrated current supply. The current supply has the ability to operate to any voltage at its output 172. The value of the resistor 170 can be used to scale the current to any desired value. Preferably, the positive feed-back circuit 174 should have the same resistance as the thermopile to balance effects of input currents to the plus and minus inputs of the operational amplifier 168. However, using for example an ICL7650S operational amplifier 168, the voltage error resulting from any imbalance is insignificant if the resistance of the thermopile 98 is relatively low; therefore no resistor is needed in the positive feedback circuit.

In an example of the operation of the pre-amplifier/current source circuit 166, assume the output S is grounded and the resistor R is 1 ohm. The plus input is at ground potential so the minus input must also be at ground potential. With a 1 millivolt output from the thermopile 98 there must be a voltage of the opposite polarity across the 1 ohm resistor R. This can only occur if a current of 1 milliamp is flowing through this resistor 170. The value of this resistor can be used to scale the current to any value. A current supply must operate into any voltage. To illustrate this assume the output 172 is operating into a 4 volt potential. The plus input is at 4 volts. Again to have the minus input at 4 volts a 1 ma current must flow through the 1 ohm resistor to balance the 1 mv output of the thermopile. It is apparent that whatever potential is at the output 1 ma must flow in the 1 ohm resistor to produce equal voltages at each input. Moreover, as the value of the output voltage of the thermopile 98 changes, there must be a proportional corresponding change in the current in the resistor R.

The pre-amplifier circuit 166 preferably operates into a voltage that is one-half the supply voltage. This is accomplished by the biased amplifier circuit 176 of the amplifier circuit 164. This amplifier 176 has a single voltage supply input $E_{supply}$. The plus input to operational amplifier 178 (which may be an LM2904 operational amplifier) is connected to a voltage divider 180 that divides the input voltage in half; therefore, the bias voltage of operational amplifier 178 is $E_{supply}/2$. Since a properly functioning operational amplifier maintains the same potential at both inputs, the minus input also is maintained at one-half the supply voltage.

To examine the functioning of the amplifier 176 assume the pre-amplifier 166 is supplying no current. The current $I_{ref}$ into the summing junction 182 from the reference voltage source $E_{ref}$ via resistor 184, which has a value of $R_{ref}$ ohms, is then $(E_{ref} - \frac{1}{2}E_{supply})/R_{ref}$. Since no current is flowing into the summing junction 182 the current in the feedback resistor 186, which has a value of $R_{feedback}$ ohms, must be $-I_{ref}$. The output voltage $E_{out}$ on output line 188 is then $E_{out} = (\frac{1}{2}E_{supply} - I_{ref}* R_{feedback})$.

Now, if the pre-amplifier 166 is supplying or sinking a current $I_{in}$, this current is seen at the summing junction 182 and must be added to $I_{ref}$ to determine the $E_{out}$ voltage on output 188. $I_{total} = (I_{in} + I_{ref})$. The output voltage $E_{out}$, then, is $I_{in} * R_{feedback}$. By proper selection of resistor values and reference voltage $E_{ref}$ it is possible to produce any desired output voltage as a function of input current $I_{in}$ from the pre-amplifier 166 and offset. Thus, it will be appreciated that the output voltage $E_{out}$ on line 188 is a representation of the voltage produced by the thermopile 98 and, therefore, of the concentration of methanol in the fuel mixture.

The output of circuit 164 illustrated in FIG. 14 is a DC signal $E_{out}$ which has an electrical value proportional to the amount of methanol in the fuel mixture contained in the sampling chamber when the lamp is cycled on to take a reading. This output signal $E_{out}$ is then fed to data processor 33, such as a vehicle's onboard computer, which may convert the electrical value to a digital form that may be utilized to control one or more parameters of engine 22 and, in particular, the fuel/air ratio. The electrical components illustrated in FIG. 14 may be mounted to and electrically connected by a printed circuit board for assembly in recess 112, except for the thermopile 98 which is separately housed in recess 82.

As above discussed, the lamp power supply circuit illustrated in FIG. 13 may be replaced by a standard voltage regulator circuit having a 12 volt input and a 9 volt output (9 volts being preferred for extended life of a 12.8 volt rated lamp). This same 9 volt voltage supply circuit may be used to supply the reference voltage $E_{ref}$ and the supply voltage $E_{supply}$ for the FIG. 14 circuit. The value of $E_{ref}$ and $E_{supply}$ may be scaled as needed by voltage dividers properly to tailor the $E_{out}$ voltage to the vehicle's onboard computer.

From the foregoing detailed description, it can be seen that the present invention provides an improved device and method for determining the methanol content of a methanol-gasoline fuel mixture. More generally, the principles of the invention may also be applied to other devices and methods for determining the amount of an energy absorbing compound in a mixture thereof with other energy absorbing compounds. In this more general application, the comparison will be between transmitted radiation in a wavelength band which is absorbed by the measured energy absorbing compound and not by the other compounds and a wavelength band which is equally absorbed by the measured and other compounds and preferably substantially unabsorbed by such compounds.

While there has been illustrated and described a preferred embodiment of the present invention, it will be understood by those skilled in the art that various changes and modifications may be made, and equivalents may be substituted for elements thereof without departing from the scope of the invention. By way of exemplary modification, other types of detectors other than the above described thermopile may be employed. By way of example, lead sulfide photoresistor type detectors may be used with one (the measuring detector) being filtered to be sensitive to light that is transmitted through the fuel mixture at 1550 nm and the other (the reference detector) at 1300 nm. The output of the two detectors may then be ratioed using for example the circuit illustrated in FIG. 15.

Figure 15:
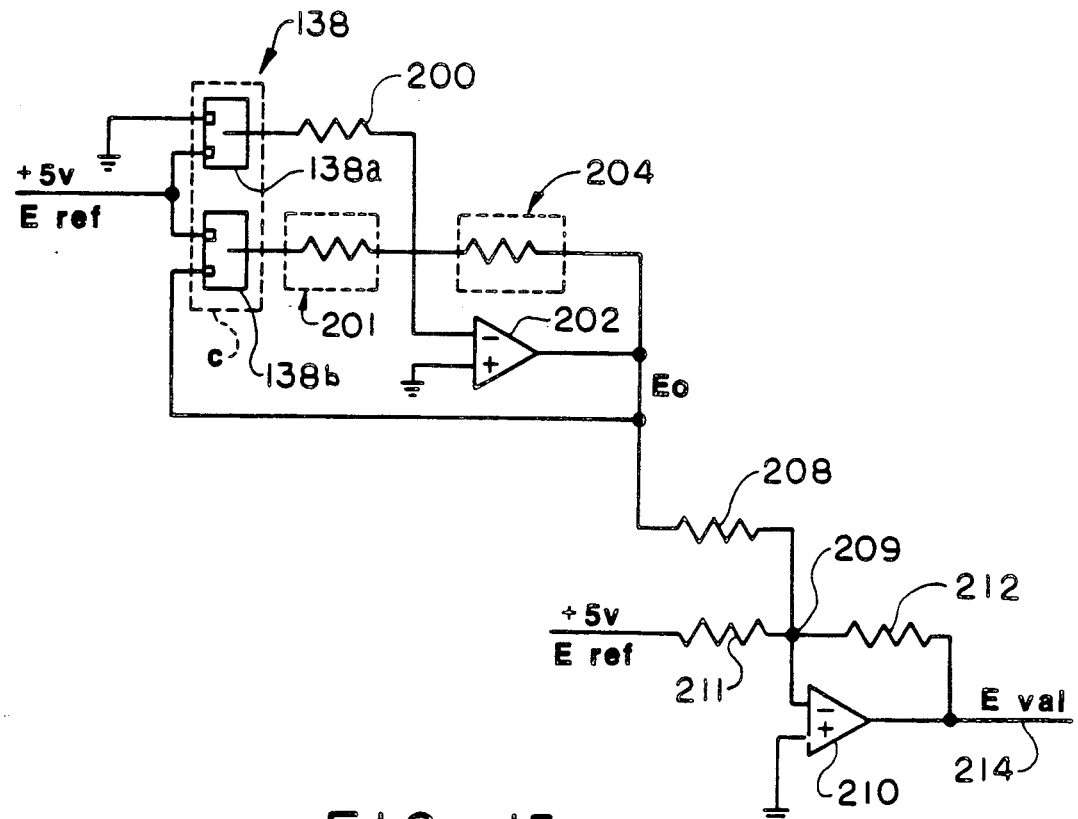
FIG. 15 is another embodiment of an output circuit useful with photoresistor detectors.

In the FIG. 15 circuit, an electronic switch, such as electronic switch 138 employed in FIG. 13 to control the supply of voltage to the lamp, provides for two operational modes. When electronic switch 138 is in a ratio or measuring mode (the lamp is on), resistor 200 is connected by electronic switch channel 138a to ground and the 1300 nm or reference detector 201 is connected by switch channel 138b to a reference voltage $E_{ref}$. The minus input of operational amplifier 202, such as an LM444AMD, will be at ground potential so no current flows through resistor 200. The plus input of operational amplifier 202 is connected to ground potential. Operational amplifier 202 operates to maintain the minus input at the same potential as the plus input, this being accomplished by adjusting the voltage $E_o$ at the output of amplifier 202. Since essentially no current flows into the minus input of amplifier 202, the current through the 1300 nm detector 201 has to equal the current through the 1550 nm detector 204. If the summing junction connected to the minus input of amplifier 202 is at ground potential, the current in the 1300 nm detector 201 is $E_{ref}/R_{1300}$, where $R_{1300}$ is the resistance of the photoresistor detector 201 filtered at 1300 nm. Since the current in the 1550 nm detector 204 is the same, the output voltage must be $1 \times R_{1550}$, where $R_{1550}$ is the resistance of the photoresistor detector 204 filtered at 1550 nm. Substituting $E_{ref}/R_{1300}$ for 1 results in Output Voltage $E_o = E_{ref} \times (R_{1550}/R_{1300})$. $E_{ref}$ is a fixed voltage so the output $E_o$ is a constant times the ratio of the two detectors. The detectors 201 and 204 may be Type 1305 lead sulfide photoresistor detectors available from Infrared Industries.

The output $E_o$ is supplied via resistor 208 to a summing junction 209 connected to the minus input of operational amplifier 210, which may be a conventional LM444AMD. The plus input of operational amplifier 210 is connected to ground potential, hence the summing junction 209 will be held at ground potential by operational amplifier 210. Summing junction 209 is also connected to a reference voltage $E_{ref}$ through resistor 211 and to the output of operational amplifier 210 via a feedback resistor 212. Since no current flows into the minus input of operational amplifier 210, the algebraic sum of all the currents of resistors 208, 211 and 212 must equal zero. Since the reference voltage $E_{ref}$ and resistor 211 have constant values, the current has a constant value. Also, the output $E_o$ of amplifier 202 is negative and the reference voltage $E_{ref}$ is positive and smaller than $E_o$. Thus, the residual current through resistor 212 is equal $I_{ratio} - I_{ref}$, where $I_{ratio}$ is the current through resistor 208 and $I_{ref}$ is the current through resistor 211. Accordingly the output $E_{val}$ of amplifier 210 on line 214 must be the resistance value of resistor 212 times ($I_{rati-}$ $o-I_{ref}$). By making the resistors 208, 211 and 212 equal in value, the output $E_{val}$ on line 214 will be equal the output of the ratio amplifier minus a constant offset value ($E_{ref}$), as may be needed to tailor the output of the sensor to the onboard computer of the vehicle.

In the other mode of electronic switch 138, (when the lamp is off) the 1300 nm detector 201 is connected to the output of operational amplifier 202 and the resistor 200 is connected to $E_{ref}$. Accordingly, the two detectors will be connected in parallel and the output of the preamplifier circuit will be proportional to a constant times the parallel resistance of the two detectors. This is useful for effecting temperature compensation.

Another type of detector assembly that may be used in place of the detector assembly 83 (although less preferred) comprises a pair of thermopiles coupled to form a differential thermopile assembly. In one form, conventional thermopile detectors, such as Model 2M thermopile detectors available from Dexter Research Center, Inc. of Dexter, Mich., are installed in respective holes in an aluminum plate in side-by-side relationship. The detector cases preferably are in thermally conductive contact with the aluminum plate which assists in maintaining the cold junctions of the detectors at the same temperature, as desired. The cold junctions or negative terminals of the detectors are electrically connected to provide a differential output voltage across the hot junction or positive terminals.

A modification of the just described detector assembly involves the use of thermopile elements such as the ceramic mounted elements of the above noted type of thermopile detectors. The ceramic mounted elements each includes a thermopile made of evaporated bismuth and antimony on a Mylar substrate which in turn is supported on a thin ceramic disk. The ceramic disk has a slit aligned with the active or sensitive area of the thermopile and the active area has an energy absorbing material such as smoke black deposited thereon. The cold junction is in thermal contact with the ceramic substrate. A pair of these elements may be secured as by cementing to an aluminum substrate like that employed in the illustrated preferred embodiment, with the slit in the ceramic substrate of each element aligned with a correspondingly sized slit in the aluminum substrate. The cold junctions of the two elements are connected together electrically and thermally to form a differential thermopile assembly. The active areas of the two elements then may be used as the measuring and reference sensing areas respectively associated with the measuring and reference wavelength bands. The resultant assembly may be mounted in the detector housing 42 in essentially the same manner as detector assembly 83. The aluminum plate functions much like a heat sink to keep the temperature of the cold junctions as close as possible.

Equivalent alterations and modifications will occur to others skilled in the art upon the reading and understanding of this specification. The present invention includes all such equivalent alterations and modifications and is limited only by the scope of the following claims.

The embodiments in which an exclusive property or privilege are claimed are defined as follows:

1. A sensor for measuring the amount of alcohol in an alcohol-gasoline fuel mixture, comprising:
    means for generating a broad band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline;
    means for receiving the alcohol-gasoline fuel mixture for passage of said first and second wavelength bands of energy through the mixture; and
    means for detecting the amount of energy remaining in the first and second wavelength bands of energy passed through the alcohol-gasoline mixture and for providing a signal related to the detected amounts of energy.

2. A sensor as set forth in claim 1, wherein said means for detecting includes a dual element thermopile having first and second sensing elements, and first and second band pass filters disposed between said means for generating and said first and second sensing elements, respectively, for passing the first and second wavelength bands.

3. A sensor as set forth in claim 2, wherein said dual element thermopile includes a plurality of serially connected thermocouples having respective hot and cold thermojunctions.

4. A sensor as set forth in claim 2, including a housing, said means for receiving including a chamber in said housing, lens means disposed between said means for generating and said chamber for causing light rays emitted by said means for generating to pass through said chamber in parallel relationship, and respective lens means for causing light rays passing from said chamber to converge onto said first and second sensing elements.

5. A sensor as set forth in claim 1, wherein said means for generating includes an incandescent lamp.

6. A sensor as set forth in claim 1, including a housing and wherein said means for receiving includes a flat walled chamber in said housing.

7. A sensor as set forth in claim 1, including a housing having a venturi with an inlet and an outlet, and said means for receiving includes a chamber in said housing connected by a first passage to said inlet of said venturi and a second passage to said outlet of said venturi.

8. A sensor as set forth in claim 1, including a housing having a first part containing said means for generating and a second part containing said means for detecting.

9. A sensor as set forth in claim 8, wherein said first and second parts have juxtaposed faces, and said means for receiving includes a chamber formed by a recess in at least one of said faces.

10. A sensor as set forth in claim 1, wherein the second wavelength band of energy will be substantially unabsorbed by both the alcohol and gasoline.

11. A sensor as set forth in claim 10, including means for converging light rays emerging from said means for receiving onto said first and second detector means.

12. A sensor as set forth in claim 11, wherein said first and second detector means include respective sensing areas, and first and second band pass filters are interposed between said means for converging and said sensing areas of said detector means.

13. A sensor as set forth in claim 11, including a housing, said means for receiving including a chamber in said housing, said housing having a wall forming one side of said chamber, and said means for converging light rays including at least one lens formed integrally in said wall.

14. A sensor as set forth in claim 10, wherein said first and second wavelength bands are centered at about 1550 nm and 1300 nm, respectively.

15. A sensor as set forth in claim 14, wherein said wavelength bands have a band width of between about 12 and 50 nm.

16. A sensor as set forth in claim 10, wherein said first wavelength band is within a range of 1450-1600 nm and said second wavelength band is within a range of 1200-1400 nm.

17. A sensor as set forth in claim 10, wherein said first and second detector means include respective sensing elements of a differential thermopile.

18. A sensor as set forth in claim 1, wherein said means for generating includes an incandescent lamp, and further including reflector means for directing the light emitted by said lamp towards said means for receiving.

19. A sensor for measuring the amount of alcohol in an alcohol-gasoline fuel mixture, comprising:
    means for generating a broad band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline;
    means for receiving the alcohol-gasoline fuel mixture for passage of said first and second wavelength bands of energy through the mixture; and
    means for detecting the amount of energy remaining in the first and second wavelength bands of energy passed through the alcohol-gasoline mixture and for providing a signal related to the detected amounts of energy,
    said means for detecting including a dual element thermopile having first and second sensing elements, and first and second band pass filters disposed between said means for generating and said first and second sensing elements, respectively, for passing the first and second wavelength bands,
    said dual element thermopile including a plurality of serially connected thermocouples having respective hot and cold thermojunctions, and
    said hot and cold thermojunctions of said thermocouples being grouped together at laterally spaced apart locations to form respective ones of said sensing elements.

20. A sensor as set forth in claim 19, wherein said hot and cold thermojunctions of said thermocouples are arranged in a respective pair of parallel rows.

21. A sensor for measuring the amount of alcohol in an alcohol-gasoline mixture, comprising:
    means for generating a wide band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline;
    means for receiving the alcohol-gasoline mixture for transmission of said first and second wavelength bands of energy through the mixture; and
    first and second detector means respectively for detecting the amount of energy remaining in the first and second wavelength bands of energy transmitted through the alcohol-gasoline mixture.

22. A sensor as set forth in claim 21, including mechanical adjustment means for adjustably varying the relative intensity of light directed towards said first and second detector means from said means for generating.

23. A sensor for measuring the amount of alcohol in an alcohol-gasoline mixture, comprising:
    means for generating a wide band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline, said means for generating including an incandescent lamp;
    means for receiving the alcohol-gasoline mixture for transmission of said first and second wavelength bands of energy through the mixture;
    first and second detector means respectively for detecting the amount of energy remaining in the first and second wavelength bands of energy transmitted through the alcohol-gasoline mixture;
    reflector means for directing light emitted by said lamp towards said means for receiving; and
    means for adjusting the relative positions of said means for receiving, lamp and reflector means to vary the relative intensity of light directed towards said first and second detector means.

24. A method for measuring the amount of alcohol in an alcohol-gasoline fuel mixture, comprising the steps of:
    generating a broad band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline;
    passing the first and second wavelength bands of energy through the alcohol-gasoline fuel mixture; and
    detecting the amount of energy remaining in the first and second wavelength bands of energy passed through the alcohol-gasoline mixture and providing a signal related to the detected amounts of energy.

25. A method as set forth in claim 24, wherein said detecting step includes using first and second sensing elements of a dual element thermopile to detect the amount of energy remaining in the first and second wavelength bands, and disposing first and second band pass filters between a broad band source of energy and the first and second sensing elements, respectively, for passing the first and second wavelength bands.

26. A sensor for measuring the amount of alcohol in an alcohol-gasoline mixture, comprising:
    means for generating a wide band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline, said means for generating including an incandescent lamp;

means for receiving the alcohol-gasoline mixture for transmission of said first and second wavelength bands of energy through the mixture; and first and second detector means respectively for detecting the amount of energy remaining in the first and second wavelength bands of energy transmitted through the alcohol-gasoline mixture, said first and second detector means respectively including first and second thermopiles each including hot and cold junctions, said hot junctions of said thermopiles forming sensing areas upon which said first and second wavelength bands of energy impinge, and said cold junctions being electrically and thermally connected.

27. A method for measuring the amount of alcohol in an alcohol-gasoline mixture, comprising:

generating a wide band of energy including a first wavelength band of energy that will be absorbed by the alcohol and substantially unabsorbed by the gasoline and a second wavelength band of energy that will be absorbed substantially equally by the alcohol and gasoline to the extent that the second wavelength band of energy is absorbed by the alcohol and gasoline;

passing the first and second wavelength bands of energy through the alcohol-gasoline mixture; and detecting the amount of energy remaining in the first and second wavelength bands of energy transmitted through the alcohol-gasoline mixture by using first and second detector elements.

28. A method for measuring the amount of alcohol in an alcohol-gasoline fuel mixture, comprising:

passing first and second wavelength bands of energy through the alcohol-gasoline fuel mixture, the first wavelength band of energy being absorbed by the alcohol and substantially unabsorbed by the gasoline and the second wavelength band of energy being absorbed substantially equally by the alcohol and gasoline to the extent that the second wavelength band of energy is absorbed by the alcohol and gasoline; and detecting the amount of energy remaining in the first and second wavelength bands of energy passed through the alcohol-gasoline mixture and providing signals related to the detected amount of energy.

* * * * *